ated Styrenes

United States Patent [19]
Daren et al.

[11] 4,292,453
[45] Sep. 29, 1981

[54] PROCESS FOR PREPARING RING HALOGENATED STYRENES

[75] Inventors: Stephen L. J. Daren, Beer Sheva; David Vofsi; Meir Asscher, both of Rehovot, all of Israel

[73] Assignee: Makhteshim Chemical Works Ltd., Beer Sheva, Israel

[21] Appl. No.: 42,159

[22] Filed: May 24, 1979

[51] Int. Cl.³ ............................................. C07C 25/14
[52] U.S. Cl. ................................. 570/193; 585/435; 585/436
[58] Field of Search ........................... 585/435, 436; 260/650 R, 654 D; 570/193

[56] References Cited
U.S. PATENT DOCUMENTS 1,870,877  8/1932  Smith et al. ........................ 585/436
3,542,888  11/1970  d'Ostrowick et al. .......... 260/650 R
3,981,937  9/1976  Campbell et al. .................. 260/655

*Primary Examiner*—Curtis R. Davis
*Attorney, Agent, or Firm*—Browdy and Neimark

[57] ABSTRACT

The present invention relates to the production of ring-halogenated styrene monomers of high purity. These are of value in the production of polymers which possess flame retardance. The process of the invention comprises reacting heterogenously ring halogenated beta-bromoethyl benzene with a strong aqueous alkali base in the presence of a quaternary phase transfer catalyst until substantially all the bromoethyl benzene has undergone reaction, separating the phases, washing and neutralizing the organic phase and recovering the ring-halogenated styrene monomer, which is the desired product.

13 Claims, 1 Drawing Figure

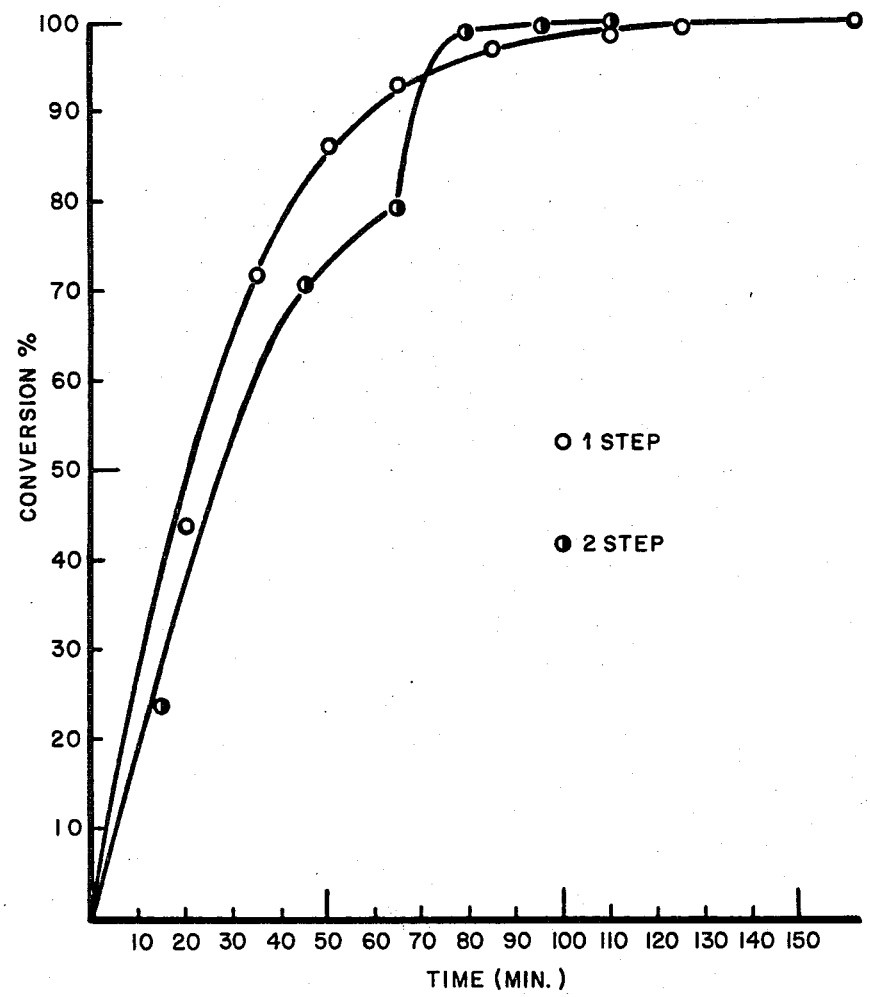

PROCESS FOR PREPARING RING HALOGENATED STYRENES

BACKGROUND OF THE INVENTION

Styrene based polymers make up a significant part of the plastics industry. Polymers having styrene as part of their structural makeup are for example polystyrene, styrene-butadiene copolymers, ABS, SAN, thermosetting polyester resins and copolymers of styrene with acrylate and maleic monomers, and many others. One great deficiency of these styrene based polymers, however, is their flammability, and there is an ever increasing awareness and interest in providing polymers which possess flame retardance.

STATE OF THE PRIOR ART

To overcome this problem numerous solutions have been proposed. One method involves blending halogen or phosphorous containing compounds or a mixture of these, with polymers and resins before or during processing into useful articles. Thus, the flame retarding material is an additive and as such is subject to leaching out of the plastic or exuding to the surface of the polymer composition and thereby causing loss of flame retardant properties. Furthermore, these additives often adversely affect the physical properties of the plastics. Another method involves incorporating a reactive flame retardant compound into the polymer chain or matrix. This method is more desirable. However, thus far the available reactive flame retardant materials have been limited and find utility in specific applications only. Compounds satisfactory in one polymer may not be suitable in another.

One particular method for introducing flame retardance to sytrene based polymers was disclosed in the literature and in patents but was never commercialized. This method consists substituting or at least partially substituting, ring halogenated styrene for styrene. The halogen is thus incorporated into the polymer chain and is not readily removed. Furthermore, the halogens on the aromatic ring are more stable and less prone to abstraction than are aliphatic halogens.

Ring halogenated styrenes are known materials and much has been published concerning their ability to impart flame retardance to plastics. The halogenated styrene monomers, however, have not been sold commercially primarily because of the uneconomical methods for preparing them. For example, U.S. Pat. No. 2,432,737 and U.S. Pat. No. 2,485,524 disclose processes for preparing dichlorostyrene. A number of patents have issued describing processes for preparing bromostyrene monomers. Thus, for example, U.S. Pat. No. 3,737,469 describes a process whereby beta-bromoethyl bromobenzene was passed over molten salts in the presence of an alphatic alcohol to product bromostyrene and methyl bromide. More recently, U.S. Pat. No. 3,980,722 claims a process for producing bromostyrene and lower alkyl bromide by pyrolizing β-bromoethyl bromobenzene in the presence of a lower alcohol at a temperature in the range of 400° C. to 550° C. without the use of catalyst.

These latter processes which represent the latest advance in the art require high temperature and give conversion rates which could be improved upon. The high temperatures required for the reaction necessitate the use of special equipment because of the corrosive nature of the halogen containing compound. Furthermore, the high temperature also produces, albeit in small quantities, undesirable side products which are difficult to eliminate from the product and which adversely influence the degree of polymerization of the desired ring halogenated styrene monomers.

Recently there was published in U.S. Pat. No. 3,992,432 a process for catalyzing heterogeneous ionic reactions in a system of multiple liquid phases in which at least two of the reactants are each located in a different phase with respect to the other with quaternary salt catalysts having a total sum of 18 to 70 carbon atoms.

These so called phase transfer reactions have become popular with organic chemists of late and a number of review articles on the subject have been written. One of these earlier reviews by Jozef Dockx, *Synthesis* August 1973, 441-56, discloses among other things the preparation of styrene from phenylethyl bromide in 50% NaOH with quaternary ammonium salt catalysts, (p.449, and 454 table 11.)

The reaction is stated to be complete within 2 hours at 90° C. This is, however, true only when the mole ratio of concentrated aqueous NaOH is very high with respect to phenylethyl bromide. With low mole ratios of concentrated NaOH to phenyl ethyl bromide, however, for example 1.5:1, conversion to styrene is only 60% after 90 minutes at 90° C. Thus, this method does not lend itself to a commercial process because the problem of working up and disposing of excessively large amounts of concentrated NaOH at the end of the process must be considered. Furthermore, since the product styrene is a reactive monomer, which is subject to auto polymerization, it is not desirable to maintain the reaction at such an elevated temperature for a longer period.

SUMMARY OF THE INVENTION

We have discovered to our surprise that ring-halogenated beta-bromoethyl benzenes can be successfully converted to stable ring halogenated styrene monomers of high purity in a fast efficient and energy conserving commercializable process comprising:

(a) reacting heterogeniously a ring halogenated β-bromoethylbenzene with strong aqueous alkali base in the presence of a phase transfer catalyst.

(b) separating the phases, (c) washing and neutralizing the organic phase and (d) recovering ring halogenated styrene monomer from the liquid organic phase.

In the absence of a quaternary catalyst the reaction virtually does not take place.

The ring halogenated β-bromoethylbenzene can be described by the following structure:

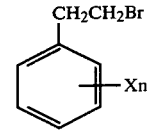

where X is halogen such as fluorine, chlorine, bromine and iodine. Preferably X is chlorine or bromine, most preferably bromine, and n is an integer from 1 to 5, preferably 1 to 3.

Typical compounds falling within this formula are the following: beta-bromoethyl-o-fluorobenzene, beta-bromoethyl p-iodobenzene, beta-bromoethyl-o-, m- or p-chlorobenzene, beta-bromoethyl-2,4-dichlorobenzene, beta-bromoethyl-3,4-dichlorobenzene, beta-bromoethyl-2,4,6-trichlorobenzene, beta-bromoethyl-3,4,5-trichlorobenzene, beta-bromoethyl-p-bromobenzene, beta-bromoethyl-o-bromobenzene, beta-bromoethyl-2,4-dibromobenzene, beta-bromoethyl-3,4-dibromo-benzene, beta-bromoethyl-2,4,5-tribromobenzene, beta-bromoethyl-2,4,6-tribromobenzene, beta-bromoethyl-2-bromo-4-chlorobenzene beta-bromoethyl pentachlorobenzene etc. and mixtures of any of these. Preferred starting materials are beta-bromoethyl-mono-bromobenzene, beta-bromoethyl-dibromobenzene, beta-bromoethyl tribromobenzene or mixture of these and beta-bromoethyl-dichlorobenzene.

The strong aqueous alkali base solutions contemplated for reacting with the ring halogenated beta-bromoethyl benzenes are usually solutions of sodium hydroxide or potassium hydroxide in concentrations of about from 20 to 50% preferably 30–45%. The mole ratio of alkali base solution to ring halogenated beta-bromoethyl benzene may be from 10:1 to 1:1, usually 5:1 to 1.5:1 and preferably 3:1 to 1.5:1. Other ratios may be used, but, for practical reasons it is desirable to use the least amount of base possible. We have found that good results may be obtained with 45% alkali base solutions even with a mole ratio of 1.5:1 alkali base to ring halogenated β-bromoethyl benzene. This ratio permits satisfactory precipitation of the alkali bromide which can be readily filtered off and the relatively small quantity of residual aqueous alkali base solution can be recycled, thus minimizing the loss and handling of excess alkali base solution.

Phase transfer catalysts suitable for the instant process are organic quaternary salts including one or more groups having the formula (AM+X⁻ where A is an organic portion of the salt molecule bonded to . . . M . . . by four covalent linkages and preferably comprising a plurality of hydrocarbon radicals of either monovalent or polyvalent character, M is selected from the group consisting of nitrogen, phosphorous, arsenic, antimony and bismuth and X⁻ is an anion which will dissociate from the cation (AM)+ in an aqueous environment. The group (AM)+X⁻ may be repeated as in the case of dibasic quaternary salts. The salt may also be polymeric in character, with the described group (AM)+X⁻ repeated a number of times. The quaternary salts of this invention may better be described by the following formula:

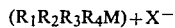

wherein M and X are as heretofore defined and R₁,R₂,R₃ and R₄ are hydrocarbon radicals (alkyl, alkenyl, aryl, alkaryl, aralkyl, cycloalkyl etc.), having 1 to 18 carbon atoms or in the case where M is nitrogen R₁ and R₂ may be hydrocarbyl groups while R₃ and R₄ may be joined to form a 5 or 6 membered heterocyclic ring having at least one quaternized nitrogen atom in the ring as the first member thereof and the remaining members of the ring are each carbon atoms; and X⁻ is an anion which will disociate in aqueous environment. The preferred anions are hydroxide, chloride and bromide but other suitable anions include, for example, fluoride, iodide, bisulfate, perchlorate, nitrate, acetate, benzoate, tosylate etc.

Quaternary ammonium compounds are, however, preferred as catalysts. Some phase transfer catalysts contemplated for the process of this invention but not limited thereto are benzyl tributyl ammonium chloride, tetrabutyl ammonium bromide, pentyl triethyl ammonium bromide, butyl triethyl ammonium bromide, propyl triethyl ammonium bromide, tricaprylyl methyl ammonium chloride, benzyl triethyl ammonium chloride, benzyl triethyl ammonium bromide, benzyltriethyl ammonium hydroxide, cetyl trimethyl ammonium chloride, myristyl trimethyl ammonium bromide, octadecyl trimethyl ammonium chloride, phenyl trimethyl ammonium bromide, tetrabutyl ammonium hydroxide, tricaprylyl methyl ammonium chloride, dodecyl trimethyl ammonium bromide, benzyl triphenyl phosphonium chloride, n-butyl triphenyl phosphonium bromide, of which the first six are preferred and the propyl, butyl and pentyl triethyl ammonium salts are most preferred.

The quaternary catalyst may be dissolved or dispersed in the organic phase and the strong aqueous alkali base slowly added to the stirring reactant. The reaction is exothermic and once the desired temperature is reached little heating is necessary to maintain the temperature. In some instances it is desirable to remove the catalyst from the final product. We have, therefore, found particularly useful quaternary ammonium salts having a partition coefficient favouring solubility in the aqueous phase during the final aqueous or dilute acidic wash of the product. Such a final aqueous wash simultaneously neutralizes the organic phase and removes catalyst therefrom: Suitable catalysts for this purpose are quaternary ammonium salts having a total of 8 to 16 carbon atoms and within this group those having 9 to 11 carbon atoms are most preferred, for example, propyl triethyl ammonium salts and butyl triethyl ammonium salts.

This aspect of removing residual catalysts from the product can be of some importance especially when the monomer has a susceptability to polymerize. Thus, for example, we found it particularly useful to remove residual catalyst from the organic phase after completion of the reaction in the case of tribromostyrene. In instances where residual catalyst was not washed out, the tribromostyrene monomer polymerized before it was possible to crystallize it. Removal of residual quaternary ammonium catalyst is therefore, most desirable in cases where its presence makes the monomer susceptible to polymerization. Once, however, the catalyst is eliminated after the reaction, the monomer is much more stable to spontaneous premature polymerization.

In the presence of even a small amount of an organic quaternary salt, the reaction in the case of ring halogenated beta-bromoethyl benzene proceeds to completion in a very short time. The exact time is of course dependent on the temperature of reaction which can range from 0° C. to 120° C. depending on the type and number of halogens substituted on the ring. For example, tribromo-ring substituted beta-bromoethyl benzene reacts quite satisfactorily at a temperature range of from 0° C. to 45° C. and preferably at room temperature. On the other hand, monobromo-ring substituted beta-bromoethylbenzene gives satisfactory reaction rates at a temperature range of 40° C. to 120° C. preferably 60° C. to 100° C. The optimum temperature for the reaction of any one ring halogenated beta-bromoethylbenzene can readily be determined in each case within the general range given above. Similarly mixtures of ring halogenated beta-bromoethylbenzenes will also have optimum temperatures somewhere within this range.

The amount of phase transfer catalyst can be anywhere from 0.1% to ;B 10% by weight of the ring halogenated β-bromoethyl benzene but between 0.25 to 3% is generally satisfactory. The process of this invention is preferably run without a solvent particularly for the preparation of monobromostyrene. However, solvents may be used when desired. Suitable solvents are the chlorinated solvents such as dichloroethylene, methylene dichloride, chloroform, carbon tetrachloride, dichlorobenzene etc., hydrocarbon solvents such as benzene, toluene, xylene, hexane, cyclohexane etc. In fact any non reactive solvent may be used.

The rate of reaction is dependent on, and increases with the concentration of aqueous alkali base, the concentration of catalyst, the temperature and the specific ring halogenated β-bromoethyl benzene. The reaction is faster the greater the number of halogens on the ring. Thus for example the rate is in the order to tribrominated dibrominated, monobrominated and unbrominated β-bromoethyl benzene. In practice, the ring halogenated β-bromoethyl benzene starting material usually contains some quantities of non-brominated β-bromoethyl benzene which during the course of the dehydrobromination reaction is transformed to ordinary styrene. The rate of this latter reaction is slower than the rate for the ring halogenated compounds and it determines to some measure the time required for completion of the reaction. In order, therefore, to prepare substantially pure ring halogenated styrene monomer free of any β-bromoethyl benzene it is necessary to continue the reaction until all of the β-bromoethyl benzene has been converted to styrene. The reason for eliminating any residual β-bromoethyl benzene from the halogenated styrene is that the β-bromoethyl benzene is a chain transfer agent and prevents the halogenated styrene monomer from being polymerized to a high molecular weight. This problem is particularly pertinent in the case of monobromostyrene because invariably the precursor, β-bromoethyl bromobenzene contains small amounts of β-bromoethyl benzene.

The method of this invention enables one to eliminate even the small quantities of β-bromoethyl benzene economically and thus provide a bromostyrene monomer of sufficient purity capable of being polymerized to a high molecular weight.

The process of this invention can further be improved by using in addition to a phase transfer catalyst small amounts of an inorganic nitrite salt such as $NaNO_2$ or $KNO_2$. The exact mechanism by which the nitrite salt operates is not understood. However, additions of as little as 0.15% nitrite based on the ring halogenated beta-bromobenzene already increase the rate of the phase transfer reaction. Generaly 0.2 to 5% by weight, nitrite salt, preferably 0.25-3%, based on the organic starting material, is sufficient to reduce the time for completion of the reaction to about ⅓ to ½ of the time necessary without nitrite.

The accelerated reaction rate effected by the nitrite salts is of particular advantage when preparing bromostyrene. These monomers are much more sensitive than ordinary styrene and are prone to auto-polymerize especially at elevated temperatures. Increasing the rate of reaction and thus shortening the reaction time reduces the risk of premature polymerization. Alternatively, because the rate of reaction is increased so significantly it becomes feasible to run the reaction at lower temperatures and still complete the reaction within a reasonable time.

Another function of the nitrite salt is that it acts as a monomer stabilizer during the reaction and reduces the amount of polymerization of bromostyrenes. Normally when reaction product containing about 5-10% dibromostyrene is stored for several hours before final workup some of the monomer polymerizes. With nitrite salts as cocatalyst in the reaction, this polymerization is eliminated or at least substantially reduced. Thus the nitrite salts act also as polymerization inhibitors while the reaction is in progress and before the product is finally worked up by wahing etc.

A further feature of this invention is to conduct the phase transfer reaction stepwise. For example, the initial reaction being conducted with a portion of the total aqueous alkali base. When this reaction is substantially completed, the aqueous phase is drawn off and the remaining portion of aqueous alkali base is added and the reaction continued to completion. In this manner, the time for completion of reaction is reduced even more. The theory behind this is apparently that the initial alkali base is used up quickly diluting the base and generating alkali bromide which slows down the reaction especially when the alkali bromide has a high concentration. By removing the aqueous phase with its alkali bromide and adding fresh solution of concentrated base the reaction continues to completion at a much faster rate. This multiple stage reaction can, of course, be two, three or more stages but we have found two stages to be satisfactory. Thus in the case of beta bromoethyl bromobenzene if 80% of the aqueous alkali is used initially and 20% for the subsequent stage it is possible to reduce the time of reaction by up to about 30%.

Another objective of this invention is to prepare simultaneously ring-halogenated styrenes and alkali bromides. The phase transfer reaction of this invention requires the use of excess aqueous alkali base some of which, in the course of the reaction, is converted to alkali bromide according to the reaction.

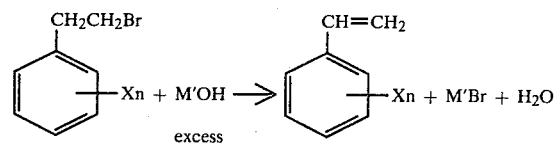

where M' is an alkali metal.

We have found that by using the proper concentration of aqueous base and a suitable mole ratio of base to organic reactant it is possible to recover, after separation of the ring halogenated styrene, alkali bromide, which precipitates in the reaction vessel by simple filtration. This alkali bromide is contaminated slightly with alkali base. However, stoichiometric addition of HBr to the precipitate converts the alkali base to alkali bromide. The alkali bromide is crystalline and satisfactory for many uses. However, high purity material can be obtained by simple recrystallization from water.

Another feature of this invention is to provide ring halogenated styrene monomers free of catalyst. Thus it is possible, at the end of the reaction after phase separation, to remove catalyst from the organic phase by washing it with dilute acid and water. Where catalyst free monomer is desired, the catalyst may be selected from compounds having a partition coefficient between the organic and aqueous phases favoring solubility in the aqueous phase.

In the enclosed FIGURE the results of addition in one step or in two of the sodium hydroxide are compared.

DESCRIPTION OF THE PREFERRED EMBODIMENT

The invention is illustrated with reference to the following illustrative examples.

EXAMPLE 1

264 g (1 m) β-bromoethyl monobromobenzene was heated in a reaction vessel together with 446 g (45%) aqueous sodium hydroxide (5 m) to 70° C. with stirring. 8 g triethylbenzyl ammonium chloride (62% aqueous solution) was added slowly and the temperature maintained at 70° C. for 160 minutes. The reaction mixture was cooled and the two phases separated. The organic upper layer was washed with dilute HCl, and water, and distilled. The product contained 148 g monobromostyrene which represents a 90% yield. Analysis by GLC of the organic phase showed 90% conversion i.e. 90% starting material was converted to bromostyrene and 10% β-bromoethyl monobromobenzene remained unconverted. Under similar reaction conditions phenylethylbromide gave a much lower conversion to styrene.

EXAMPLE 2

187.6 g of a 40% aqueous KOH solution was heated to 80° C. with stirring. To this was added 139 g of a mixture of ortho-and para-β-bromoethyl bromobenzene containing 0.8% (by weight) tricaprylyl methyl ammonium chloride over a period of a few minutes and the temperature maintained at 80° C. for two hours. During this period KBr precipitated out. The reaction mixture was then cooled to 10° C. and the KBr filtered yielding 38 g KBr and a two phase filtrate which was separated. The lower organic phase, 95 g, was washed with dilute acid and water and contained 92% monobromostyrenes. When distilled it had a boiling point 46° C. at 1 mm pressure. The KBr was dissolved in water, filtered and neutralized with dilute aqueous HBr and then evaporated. The resulting KBr precipitate was of photographic grade purity.

EXAMPLE 3

396 g (1.5 moles) of ring brominated β-bromoethyl benzene having a composition of 93% β-bromoethyl monobromo benzene 5% β-bromoethyl dibromo benzene and about 2% β-bromoethyl benzene were introduced into a rection vessel equipped with stirrer, thermometer and addition funnel. 200 g 45% aqueous sodium hydroxide (2.25 m) and 12 g sodium nitrite were added and the heterogeneous mixture heated to 80° C. and stirred vigorously. 8.5 g tributylbenzyl ammonium chloride (70% solution in water) was slowly introduced into the stirring mixture by drip feeding over 15 minutes. The temperature rose to 100° C. After 60 minutes, all the ring brominated β-bromoethyl benzene disappeared as analyzed by GLC. The reaction mixture is cooled to room temperature and 3 phases are obtained, the upper organic, the middle aqueous and the lower solid precipitated NaBr. To this mixture is added 15% aqueous HBr sufficient to neutralize the aqueous phase and bring the solid phase into solution. The organic and aqueous phases are then separated. The organic phase is washed with dilute HCl twice then with water and distilled under reduced pressure. The aqueous phase is evaporated and the sodium bromide recovered. The reaction gave 100% conversion and 90% yield. The distilled product contained 98% brominated styrene and 2% styrene.

EXAMPLE 4

1,050 g of a 49% aqueous KOH solution was heated to 100° C. with stirring. To this was added 1000 g of a crude mixture of ortho-and-para-β-bromoethyl bromobenzene and 0.7% tricaprylyl methyl ammonium chloride. Said mixture was obtained directly from the bromination of β-bromoethyl benzene without further distillation or purification of the brominated product and contains about 80% β-bromoethyl monobromobenzene. The reaction was continued at 80° C. for 90 minutes.

The temperature was then lowered to 10° C. and KBr was filtered off yielding 385 g KBr. The two phase filtrate was separated and the organic phase 670 g contained 66% of a mixture of ortho-and-para-bromostyrene. Upon washing the organic phase with dilute acid and water and distillation the monobromostyrene was recovered. The KBr was treated in a similar manner as in Example 2.

EXAMPLE 5

400 g 50% aqueous NaOH solution was stirred at room temperature and 422 g of β-bromoethyl tribromo benzene dissolved in 200 g methylene dichloride containing also 3.5 g (0.5%) triethyl benzyl ammonium chloride (64% aqueous solution) was added as was 4 g sodium nitrite. The mixture was stirred at 30° C. for 10 hours. The two phases were then separated and the organic phase washed with dilute acid to pH 5. The solvent was stripped and the product recrystallized from methanol to give tribromostyrene having a melting point 66° C.

EXAMPLE 6

To show the effect of phase transfer catalyst concentration Example 5 was repeated but without the addition of sodium nitrite and with varying catalyst concentrations.

| % Catalyst | % Conversion after 90 minutes |
| --- | --- |
| 0.5 | ~10% |
| 3 | 65% |
| 5 | 96% |

The % conversion was determined by GLC analysis.

EXAMPLE 7

Similarly reactions were run at 70° C. as follows:
β-bromoethyl bromobenzene-1 mole
Sodium hydroxide 50% (aqueous)-5 moles
Sodium nitrite as indicated in table
Triethyl benzyl ammonium chloride as in table
Conversion after 60 minutes was determined by GLC.

| % Sodium nitrite | With 1.3% catalyst % Conversion after 60 min. | With 1.8% catalyst % Conversion after 60 min. |
| --- | --- | --- |
| 0 | 45% | 63% |
| 1% | 77% | 95% |
| 2% | 98% | 100% |

EXAMPLE 8

226 g of 44.2% aqueous sodium hydroxide solution (2.5 m) was heated and stirred at 70° C. To this was added 254 g of a mixture of ring chlorinated β-bromoethyl benzene comprising about 70% dichloro-20% monochloro-and 10% trichloro-ring substitution and 9.4 g triethylbenzyl ammonium chloride (61.5% aqueous solution) as well as 5.08 g sodium nitrite. The temperature was maintained for 2 hours. After separation of the phases on cooling, the organic phase yielded chlorostyrene with a conversion rate of 80%.

EXAMPLE 9

Similarly to Example 1 bromostyrene was prepared using 0.1% tetrabutyl ammonium hydroxide as catalyst. After 90 minutes at 80° C. the conversion was 90%.

EXAMPLE 10

In a 500 ml 3 necked flask with mechanical stirrer 264 g beta-bromophenylethyl bromide containing 2% beta bromoethyl benzine containing quaternary ammonium salt, catalyst and NaNO$_2$, was stirred at 70° C. Aqueous 45% NaOH was added and the exotherm raised the temperature to 90° C. Heat was applied to maintain the temperature at 95° C. The reaction was deemed complete when the beta bromoethyl benzene disappeared on GLC analysis.

The concentration of catalyst (w/w), molar ratio of base to organic reactant, time to completion and % yield are tabulated for two catalysts, tricaprylyl methylammonium chloride (A) and butyl triethyl ammonium bromide (B).

| R.A.C. | % Q.A.C. w/w βBrBr | % NaNO$_2$ w/w βBrBr | Molar Ratio NaOH/ βBrBr | Reaction Time (hrs) | % Yield |
|---|---|---|---|---|---|
| (A) | 1.5% | 3% | 1.5 | 1.75 | 86% |
| (B) | 1.5% | 3% | 1.5 | 1.5 | 88% |
| (A) | 1.5% | 0.5% | 1.5 | >2.00 | 92% |
| (B) | 1.5% | 0.5% | 1.5 | 2.00 | 93% |
| (A) | 1.5% | 0.5% | 1.7 | 2.00 | 91% |
| (B) | 1.0% | 0.5% | 1.7 | >2 | 94% |

This example demonstrates the significant increase in yield the preferred catalyst (B) gives when compared with catalyst (A) and in a shorter time.

EXAMPLE 11

A 2 step reaction was conducted wherein 792 g (3 moles) of beta-bromoethyl-bromobenzene (containing 3% betabromoethyl benzene) was reacted with 410 g 45% NaOH (4.5 m) and 13.6 g (15%) tricaprylyl methyl ammonium chloride and 26 g (3%) NaNO$_3$ at 90° C. Initially 80% of the 45% aqueous NaOH was added to the betabromoethyl bromobenzene-catalyst mixture and the reaction maintained for 65 minutes. The reaction was then stopped and the lower aqueous phase separated. The remaining 20% aqueous NaOH was added to the organic portion and the reaction contained at 90° C. After only 45 additional minutes the reaction was complete as indicated by the disappearance of the beta-bromoethyl benzene peak, measured by GLC.

The same reaction wherein all the aqueous sodium hydroxide was introduced initially took 150 to completion. It is stressed that it is very important to have the reaction go to completion so that all the starting material is converted. This is illustrated with reference to the enclosed Figure which compares the results obtained by adding the entire sodium hydroxide at the beginning or in two steps.

We claim:

1. A process for preparing ring halogenated styrene monomers which comprises:
    (a) reacting heterogenously ring halogenated beta-bromoethyl benzene with a strong aqueous alkali base in the presence of a quarternary phase transfer catalyst including a catalytic quantity of an inorganic nitrite salt reaction accelerator until substantially all the bromoethyl benzene has been converted to ring halogenated styrene monomer;
    (b) separating the different phases,
    (c) washing and neutralizing the organic phase, and
    (d) recovering said ring halogenated styrene monomer.

2. A process according to claim 1, wherein the concentration of the strong aqueous base is 20% to 50% by weight and the base is selected from the group consisting of NaOH and KOH.

3. A process according to claim 1, wherein the mole ratio of the base to the ring halogenated beta-bromoethyl benzene is from 10:1 to 1.5:1.

4. A process according to claim 1, wherein the quaternary phase transfer catalyst is selected from quaternary ammonium salts and same is used in amounts of from 0.01% to 10% by weight calculated on the basis of ring halogeanted beta-bromo ethylbenzene.

5. A process according to claim 1, wherein the reaction is carried out at a temperature from 20° C. to 120° C.

6. A process according to claim 1, wherein the reaction is conducted in a plurality of stages, wherein spent aqueous alkali base is withdrawn and fresh aqueous alkali base is added.

7. A process according to claim 1, wherein the ring halogeanted beta-bromoethylbenzene is selected from the group consisting of betabromoethyl-ortho, -meta- and para-bromobenzenes; beta bromoethyl dibromobenzenes; beta-bromoethyl tribromobenzenes and mixtures of these; beta-bromoethyl-monochloro-dichloro, and trichlorobenzenes and mixtures of these.

8. A process according to claim 4, wherein the quaternary ammonium salt is selected from the group consisting of propyl triethyl ammonium, butyl triethyl ammonium, pentyl triethyl ammonium, tetrabutyl ammonium, tricaprylyl methyl ammonium and tributyl benzyl ammonium salts.

9. A process according to claim 4, wherein the quaternary ammonium halide has a partition coefficient favoring the aqueous phase.

10. A process according to claim 1, wherein the feedstock ring halogenated beta-bromoethyl benzene is the crude product obtained by halogenating β-bromoethylbenzene.

11. A process according to claim 1, wherein KOH is used as the strong alkali base and photographic grade KBr is recovered in addition to ring halogenated styrene.

12. A process according to claim 1, wherein the nitrite salt is selected from the group consisting of sodium nitrite and potassium nitrite and the quantities are from 0.05% to 5% calculated on the weight of the ring halogenated beta-bromoethyl benzene.

13. A process for preparing bromostyrene monomer said monomer being able to undergo polymerization to a high molecular weight polymer, which process comprises reacting beta-bromoethyl bromobenzene with 1.5 to 5 moles of a 30% to 50% aqueous alkali base in the presence of 0.1 to 5% of a phase transfer quaternary ammonium salt catalyst and 0.1-3% inorganic nitrite salt cocatalyst at a temperature from 60°-100° C. until all betabromoethyl bromo-benzene has been converted to the corresponding bromo-styrene, and recovering said bromostyrene.

* * * * *

UNITED STATES PATENT AND TRADEMARK OFFICE
CERTIFICATE OF CORRECTION

PATENT NO. : 4,292,453
DATED : September 29, 1981
INVENTOR(S) : DAREN et al

It is certified that error appears in the above-identified patent and that said Letters Patent are hereby corrected as shown below:

[75] Inventors: Stephen L.J. Daren, Rahamime Clement Claude Levy
Freddy Cohen-Jonathan, all of Beer Sheva;
David Vofsi, Meir Asscher, both of Rehovot;
all of Israel

[73] Assignee: Makhteshim Chemical Works Ltd., Beer Sheva, Israel; a part interest.

Signed and Sealed this

Twentieth Day of July 1982

[SEAL]

Attest:

GERALD J. MOSSINGHOFF

Attesting Officer — Commissioner of Patents and Trademarks